(12) United States Patent
Patel et al.

(10) Patent No.: US 10,716,612 B2
(45) Date of Patent: Jul. 21, 2020

(54) ELECTROSURGICAL DEVICE WITH MULTIPLE MONOPOLAR ELECTRODE ASSEMBLY

(71) Applicant: MEDTRONIC ADVANCED ENERGY LLC, Minneapolis, MN (US)

(72) Inventors: Bhavesh Patel, Minneapolis, MN (US); Joseph Sylvester, Minneapolis, MN (US); David Hubelbank, Minneapolis, MN (US); Stephen Polgar, Minneapolis, MN (US); William Siopes, Minneapolis, MN (US); Rajan Patel, Minneapolis, MN (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 582 days.

(21) Appl. No.: 15/375,559

(22) Filed: Dec. 12, 2016

(65) Prior Publication Data

US 2017/0172646 A1    Jun. 22, 2017

Related U.S. Application Data

(60) Provisional application No. 62/269,235, filed on Dec. 18, 2015.

(51) Int. Cl.
*A61B 18/14* (2006.01)
*A61B 18/16* (2006.01)
(Continued)

(52) U.S. Cl.
CPC ........ *A61B 18/1206* (2013.01); *A61B 18/042* (2013.01); *A61B 18/14* (2013.01);
(Continued)

(58) Field of Classification Search
CPC ... A61B 18/042; A61B 18/1206; A61B 18/14; A61B 18/1402; A61B 18/16;
(Continued)

(56) References Cited

U.S. PATENT DOCUMENTS 2,888,928 A    4/1957  Seiger
3,223,088 A   12/1965  Barber et al.
(Continued)

FOREIGN PATENT DOCUMENTS

EP    0 544 274     11/1992
JP    62/204739      9/1987
(Continued)

OTHER PUBLICATIONS

Reexam Cert 4794 For 5,697,536, Jun. 10, 2003, Eggers et al.
(Continued)

*Primary Examiner* — Michael F Peffley
*Assistant Examiner* — Amanda L Zink
(74) *Attorney, Agent, or Firm* — Dicke, Billig & Czaja, PLLC

(57) ABSTRACT

An electrosurgical device having a handpiece including a controller and an electrode assembly extending from the handpiece is disclosed. The electrode assembly includes a monopolar blade and a monopolar electrode. The monopolar blade includes a conductive element partially coated with an insulator and electrically coupled to the controller to selectively deliver a monopolar radiofrequency (RF) cutting signal. The monopolar electrode is spaced apart and electrically isolated from the monopolar blade. The monopolar electrode includes an exposed major conductive surface electrically coupled to the controller to selectively deliver a monopolar RF hemostatic sealing signal with a dispersed fluid.

35 Claims, 6 Drawing Sheets

(51) Int. Cl.
*A61B 18/12* (2006.01)
*A61B 18/04* (2006.01)
*A61B 18/00* (2006.01)

(52) U.S. Cl.
CPC .......... *A61B 18/1402* (2013.01); *A61B 18/16* (2013.01); *A61B 2018/00029* (2013.01); *A61B 2018/0063* (2013.01); *A61B 2018/00083* (2013.01); *A61B 2018/0094* (2013.01); *A61B 2018/00136* (2013.01); *A61B 2018/00154* (2013.01); *A61B 2018/00178* (2013.01); *A61B 2018/00565* (2013.01); *A61B 2018/00589* (2013.01); *A61B 2018/00595* (2013.01); *A61B 2018/00601* (2013.01); *A61B 2018/00607* (2013.01); *A61B 2018/00922* (2013.01); *A61B 2018/1253* (2013.01); *A61B 2018/1412* (2013.01)

(58) Field of Classification Search
CPC ........... A61B 2018/00029; A61B 2018/00083; A61B 2018/00136; A61B 2018/00154; A61B 2018/00178; A61B 2018/00565; A61B 2018/00589; A61B 2018/00595; A61B 2018/00601; A61B 2018/00607; A61B 2018/0063; A61B 2018/00922; A61B 2018/0094; A61B 2018/1253; A61B 2018/1412
See application file for complete search history.

(56) References Cited

U.S. PATENT DOCUMENTS

| | | | |
|---|---|---|---|
| 3,682,130 A | 8/1972 | Jeffers |
| 3,750,650 A | 8/1973 | Ruttgers |
| 3,955,284 A | 5/1976 | Balson |
| 4,014,342 A | 3/1977 | Staub et al. |
| 4,195,637 A | 4/1980 | Gruntzig et al. |
| 4,207,897 A | 6/1980 | Loyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | Van Gerven |
| 4,321,931 A | 3/1982 | Hon |
| 4,342,218 A | 8/1982 | Fox |
| 4,355,642 A | 10/1982 | Alfemess |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Scrochenko |
| 4,708,126 A | 11/1987 | Toda et al. |
| 4,736,749 A | 4/1988 | Lundback |
| 4,779,611 A | 10/1988 | Grooters et al. |
| 4,802,475 A | 2/1989 | Weshahy |
| 4,878,493 A | 11/1989 | Pasternak et al. |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,985,030 A | 1/1991 | Melzer et al. |
| 4,998,933 A | 3/1991 | Eggers et al. |
| 5,112,299 A | 5/1992 | Pascaloff |
| 5,167,659 A | 12/1992 | Ohtomo et al. |
| 5,190,541 A | 3/1993 | Abele et al. |
| 5,195,959 A | 3/1993 | Smith |
| 5,230,704 A | 7/1993 | Moberg et al. |
| 5,234,428 A | 8/1993 | Kaufman |
| 5,254,117 A | 10/1993 | Rigby et al. |
| 5,275,609 A | 1/1994 | Pingleton et al. |
| 5,281,215 A | 1/1994 | Midler |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,352,222 A | 10/1994 | Rydell et al. |
| 5,353,783 A | 10/1994 | Nakao et al. |
| 5,354,258 A | 10/1994 | Dory |
| 5,361,752 A | 11/1994 | Moll et al. |
| 5,376,078 A | 12/1994 | Dinger et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,348 A | 4/1995 | Anspach et al. |
| 5,405,376 A | 4/1995 | Mulier et al. |
| 5,409,483 A | 4/1995 | Campbell et al. |
| 5,413,556 A | 5/1995 | Whittingham |
| 5,417,709 A | 5/1995 | Slater |
| 5,423,807 A | 6/1995 | Mlilder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stem et al. |
| 5,443,470 A | 8/1995 | Stem et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,492,527 A | 2/1996 | Glowa et al. |
| 5,496,271 A | 3/1996 | Burton et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,500 A | 4/1996 | Webb et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,562 A | 7/1996 | Giter |
| 5,540,708 A | 7/1996 | Lim et al. |
| 5,542,196 A | 8/1996 | Hirsch et al. |
| 5,542,945 A | 8/1996 | Fritzsch |
| 5,545,195 A | 8/1996 | Lennox et al. |
| 5,545,200 A | 8/1996 | West et al. |

(56) References Cited

U.S. PATENT DOCUMENTS

| | | |
|---|---|---|
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Sliwa, Jr. et al. |
| 5,560,373 A | 10/1996 | DeSantis |
| 5,562,702 A | 10/1996 | Huitema et al. |
| 5,562,720 A | 10/1996 | Stem et al. |
| 5,569,241 A | 10/1996 | Edwards |
| 5,569,243 A | 10/1996 | Kortenbach et al. |
| 5,569,254 A | 10/1996 | Carlson et al. |
| 5,571,088 A | 11/1996 | Lennox et al. |
| 5,571,215 A | 11/1996 | Sterman et al. |
| 5,573,424 A | 11/1996 | Poppe |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |
| 5,605,539 A | 2/1997 | Buelna et al. |
| 5,607,462 A | 3/1997 | Imran |
| 5,609,573 A | 3/1997 | Sandock |
| 5,617,854 A | 4/1997 | Munsif |
| 5,620,415 A | 4/1997 | Lucey et al. |
| 5,620,447 A | 4/1997 | Smith et al. |
| 5,630,837 A | 5/1997 | Crowley |
| 5,643,197 A | 7/1997 | Brucker et al. |
| 5,647,869 A | 7/1997 | Goble et al. |
| 5,656,029 A | 8/1997 | Imran et al. |
| 5,658,278 A | 8/1997 | Imran et al. |
| 5,637,090 A | 9/1997 | McGee et al. |
| 5,671,747 A | 9/1997 | Connor |
| 5,672,153 A * | 9/1997 | Lax ............... A61B 10/0233 604/22 |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,294 A | 10/1997 | Osborne et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,700,262 A * | 12/1997 | Acosta ............ A61B 18/148 606/48 |
| 5,702,390 A | 12/1997 | Austin et al. |
| 5,712,543 A | 1/1998 | Sjostrom |
| 5,713,942 A | 2/1998 | Stem |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,743,903 A | 4/1998 | Stem et al. |
| 5,755,760 A | 5/1998 | Maguire et al. |
| 5,766,167 A | 6/1998 | Eggers et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,792,167 A | 8/1998 | Kablik et al. |
| 5,797,905 A | 8/1998 | Fleischman et al. |
| 5,797,960 A | 8/1998 | Stevens et al. |
| 5,735,290 A | 9/1998 | Nelson et al. |
| 5,800,428 A | 9/1998 | Nelson et al. |
| 5,800,482 A | 9/1998 | Pomeranz et al. |
| 5,810,764 A | 9/1998 | Eggers et al. |
| 5,810,802 A | 9/1998 | Panescu et al. |
| 5,810,809 A | 9/1998 | Rydell |
| 5,814,044 A | 9/1998 | Hooven |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A | 12/1998 | Tu et al. |
| 5,844,349 A | 12/1998 | Oakley et al. |
| 5,846,187 A | 12/1998 | Wells et al. |
| 5,846,191 A | 12/1998 | Wells et al. |
| 5,849,023 A | 12/1998 | Mericle |
| 5,849,028 A | 12/1998 | Chen |
| 5,861,021 A | 1/1999 | Thome et al. |
| 5,871,523 A | 2/1999 | Fleischman et al. |
| 5,871,525 A | 2/1999 | Edwards et al. |
| 5,873,845 A | 2/1999 | Cline et al. |
| 5,873,855 A | 2/1999 | Eggers et al. |
| 5,873,886 A | 2/1999 | Larsen et al. |
| 5,876,399 A | 3/1999 | Chia et al. |
| 5,879,295 A | 3/1999 | Li et al. |
| 5,879,296 A | 3/1999 | Ockuly et al. |
| 5,879,348 A | 3/1999 | Owens et al. |
| 5,881,732 A | 3/1999 | Sung et al. |
| 5,882,346 A | 3/1999 | Pomeranz et al. |
| 5,885,278 A | 3/1999 | Fleischman |
| 5,891,142 A | 4/1999 | Eggers et al. |
| 5,893,848 A | 4/1999 | Negus et al. |
| 5,895,355 A | 4/1999 | Schaer |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,899,915 A | 5/1999 | Saadat |
| 5,902,289 A | 5/1999 | Swartz et al. |
| 5,904,681 A | 5/1999 | West, Jr. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,913,854 A | 6/1999 | Maguire et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,925,045 A | 7/1999 | Reimels et al. |
| 5,927,284 A | 7/1999 | Borst et al. |
| 5,931,810 A | 8/1999 | Grabek |
| 5,931,848 A | 8/1999 | Saadat |
| 5,935,123 A | 8/1999 | Edwards et al. |
| 5,944,715 A | 8/1999 | Goble et al. |
| 5,928,191 A | 9/1999 | Houser et al. |
| 5,954,661 A | 9/1999 | Greenspon et al. |
| 5,954,686 A * | 9/1999 | Garito ............... A61B 18/12 604/37 |
| 5,975,919 A | 9/1999 | Laufer |
| 5,971,980 A | 10/1999 | Sherman |
| 5,971,983 A | 10/1999 | Lesh |
| 5,980,516 A | 11/1999 | Mulier et al. |
| 5,989,248 A | 11/1999 | Tu et al. |
| 5,993,412 A | 11/1999 | Deily et al. |
| 5,993,447 A | 11/1999 | Blewett et al. |
| 6,004,316 A | 12/1999 | Laufer |
| 6,004,319 A | 12/1999 | Goble et al. |
| 6,007,499 A | 12/1999 | Martin et al. |

(56) References Cited

U.S. PATENT DOCUMENTS

| | | |
|---|---|---|
| 6,010,500 A | 1/2000 | Sherman et al. |
| 6,012,457 A | 1/2000 | Lesh |
| 6,015,391 A | 1/2000 | Rishton et al. |
| 6,016,811 A | 1/2000 | Knopp et al. |
| 6,018,676 A | 1/2000 | Davis et al. |
| 6,019,757 A | 2/2000 | Scheldrup |
| 6,024,733 A | 2/2000 | Eggers et al. |
| 6,030,381 A | 2/2000 | Jones et al. |
| 6,036,687 A | 3/2000 | Laufer et al. |
| 6,042,556 A | 3/2000 | Beach et al. |
| 6,042,593 A | 3/2000 | Storz et al. |
| 6,048,333 A | 4/2000 | Lennox et al. |
| 6,053,923 A | 4/2000 | Veca et al. |
| 6,056,744 A | 5/2000 | Edwards |
| 6,056,745 A | 5/2000 | Panescu et al. |
| 6,056,746 A | 5/2000 | Goble |
| 6,056,747 A | 5/2000 | Saadat et al. |
| 6,066,139 A | 5/2000 | Ryan et al. |
| 6,068,653 A | 5/2000 | LaFontaine |
| 6,083,237 A | 7/2000 | Huitema et al. |
| 6,086,585 A | 7/2000 | Hovda et al. |
| 6,113,596 A | 9/2000 | Hooven et al. |
| 6,117,101 A | 9/2000 | Diederich et al. |
| 6,120,496 A | 9/2000 | Whayne et al. |
| 6,141,576 A | 10/2000 | Littmann et al. |
| 6,142,993 A | 11/2000 | Whayne et al. |
| 6,142,994 A | 11/2000 | Swanson et al. |
| 6,149,620 A | 11/2000 | Baker et al. |
| 6,152,920 A | 11/2000 | Thompson et al. |
| 6,161,543 A | 12/2000 | Cox et al. |
| 6,165,174 A | 12/2000 | Jacobs et al. |
| 6,190,384 B1 | 2/2001 | Ouchi |
| 6,193,716 B1 | 2/2001 | Shannon, Jr. |
| 6,210,406 B1 | 4/2001 | Webster |
| 6,210,410 B1 | 4/2001 | Farin et al. |
| 6,210,411 B1 | 4/2001 | Hofmann et al. |
| 6,212,426 B1 | 4/2001 | Swanson |
| 6,224,592 B1 | 5/2001 | Eggers et al. |
| 6,231,518 B1 | 5/2001 | Grabek et al. |
| 6,231,591 B1 | 5/2001 | Desai |
| 6,235,020 B1 | 5/2001 | Cheng et al. |
| 6,237,605 B1 | 5/2001 | Vaska et al. |
| 6,238,347 B1 | 5/2001 | Nix et al. |
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,283,988 B1 | 9/2001 | Laufer et al. |
| 6,283,989 B1 | 9/2001 | Laufer et al. |
| 6,296,638 B1 | 10/2001 | Davison et al. |
| 6,299,633 B1 | 10/2001 | Laufer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,956 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,494,892 B1 | 12/2002 | Ireland et al. |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,517,536 B2 | 2/2003 | Hooven et al. |
| 6,537,248 B2 | 3/2003 | Mulier |
| 6,537,272 B2 | 3/2003 | Hoey |
| 6,558,382 B2 | 5/2003 | Jahns |
| 6,558,385 B1 | 5/2003 | Bloom et al. |
| 6,575,969 B1 | 6/2003 | Rittman, III et al. |
| 6,579,288 B1 | 6/2003 | Swanson et al. |
| 6,585,732 B2 | 7/2003 | Mulier |
| 6,602,248 B1 | 8/2003 | Sharps et al. |
| 6,603,988 B2 | 8/2003 | Dowlatshahi |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Komerup |
| 6,682,501 B1 | 1/2004 | Nelson |
| 6,689,131 B2 | 2/2004 | McClurken |
| 6,702,810 B2 | 3/2004 | McClurken et al. |
| 6,706,038 B2 | 3/2004 | Francischelli |
| 6,706,039 B2 | 3/2004 | Mulier |
| 6,716,211 B2 | 4/2004 | Mulier |
| 6,716,215 B1 | 4/2004 | David et al. |
| 6,736,810 B2 | 5/2004 | Hoey |
| 6,752,816 B2 | 6/2004 | Culp et al. |
| 6,755,827 B2 | 6/2004 | Mulier |
| 6,764,487 B2 | 7/2004 | Mulier |
| 6,766,817 B2 | 7/2004 | da Silva |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | Bloom et al. |

(56) References Cited

U.S. PATENT DOCUMENTS

| | | |
|---|---|---|
| 6,960,205 B2 | 11/2005 | Jahns |
| 6,962,589 B2 | 11/2005 | Mulier |
| 6,979,332 B2 | 12/2005 | Adams |
| 7,018,241 B2 | 3/2006 | Caveney et al. |
| 7,048,687 B1 | 5/2006 | Reuss et al. |
| 7,066,586 B2 | 6/2006 | da Silva |
| 7,156,845 B2 | 1/2007 | Mulier et al. |
| 7,166,106 B2 | 1/2007 | Bartel et al. |
| 7,179,255 B2 | 2/2007 | Lettice et al. |
| 7,207,471 B2 | 4/2007 | Heinrich et al. |
| 7,232,440 B2 | 6/2007 | Dumbauld et al. |
| 7,237,990 B2 | 7/2007 | Deng |
| 7,247,155 B2 | 7/2007 | Hoey et al. |
| 7,247,161 B2 | 7/2007 | Johnston et al. |
| 7,261,711 B2 | 8/2007 | Mulier et al. |
| 7,276,074 B2 | 10/2007 | Adams et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,445,436 B2 | 11/2008 | Mittelstein et al. |
| 7,537,595 B2 | 5/2009 | McClurken |
| 7,604,635 B2 | 10/2009 | Bloom et al. |
| 7,645,277 B2 | 1/2010 | Bloom et al. |
| 7,651,494 B2 | 1/2010 | Bloom et al. |
| 7,736,361 B2 | 6/2010 | Palanker et al. |
| 7,776,014 B2 | 8/2010 | Visconti et al. |
| 7,815,634 B2 | 10/2010 | Bloom et al. |
| 7,909,820 B2 | 3/2011 | Lipson et al. |
| 7,918,852 B2 | 4/2011 | Tullis et al. |
| 7,942,872 B2 | 5/2011 | Ein-Gal |
| 7,976,544 B2 | 7/2011 | McClurken et al. |
| 7,993,337 B2 | 8/2011 | Lesh |
| 7,997,278 B2 | 8/2011 | Utley et al. |
| 7,998,140 B2 | 8/2011 | McClurken |
| 8,034,071 B2 | 10/2011 | Scribner et al. |
| 8,038,670 B2 | 10/2011 | McClurken |
| 8,048,070 B2 | 11/2011 | O'Brien et al. |
| 8,083,736 B2 | 12/2011 | Bloom et al. |
| 8,109,956 B2 | 2/2012 | Shadeck |
| 8,172,828 B2 | 4/2012 | Chang et al. |
| 8,177,783 B2 | 5/2012 | Davison et al. |
| 8,202,288 B2 | 6/2012 | Adams et al. |
| 8,216,233 B2 | 7/2012 | McClurken et al. |
| 8,323,276 B2 | 12/2012 | Palanker et al. |
| 8,348,946 B2 | 1/2013 | McClurken et al. |
| 8,361,068 B2 | 1/2013 | McClurken |
| 8,388,642 B2 | 3/2013 | Munietal |
| 8,414,572 B2 | 4/2013 | Davison et al. |
| 8,475,455 B2 | 7/2013 | McClurken et al. |
| 8,562,598 B2 | 10/2013 | Falkenstein et al. |
| 8,568,409 B2 | 10/2013 | O'Brien et al. |
| 8,632,533 B2 | 1/2014 | Greeley et al. |
| 8,882,756 B2 | 11/2014 | Greeley et al. |
| 8,906,012 B2 | 12/2014 | Conley et al. |
| 8,920,417 B2 | 12/2014 | Conley et al. |
| 8,979,842 B2 | 3/2015 | McNall, III et al. |
| 8,992,524 B1 | 3/2015 | Ellman |
| 2001/0032002 A1 | 10/2001 | McClurken et al. |
| 2001/0047183 A1 | 11/2001 | Privitera et al. |
| 2002/0038129 A1 | 3/2002 | Peters et al. |
| 2002/0049483 A1 | 4/2002 | Knowlton |
| 2002/0062131 A1 | 5/2002 | Gallo, Sr. |
| 2002/0082643 A1 | 6/2002 | Kammerer et al. |
| 2002/0165541 A1 | 11/2002 | Whitman |
| 2002/0198519 A1 | 12/2002 | Qin et al. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0097129 A1 | 5/2003 | Davison et al. |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0204679 A1 | 10/2004 | Visconti et al. |
| 2004/0215183 A1 | 10/2004 | Hoey |
| 2004/0220560 A1 | 11/2004 | Briscoe |
| 2004/0236322 A1 | 11/2004 | Mulier |
| 2004/0243163 A1 | 12/2004 | Casiano et al. |
| 2004/0267326 A1 | 12/2004 | Ocel |
| 2005/0010095 A1 | 1/2005 | Stewart et al. |
| 2005/0037672 A1 | 2/2005 | Caveney et al. |
| 2005/0069437 A1 | 3/2005 | Mittelstein et al. |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0171525 A1 | 8/2005 | Rioux et al. |
| 2005/0209564 A1 | 9/2005 | Bonner |
| 2005/0222566 A1 | 10/2005 | Nakahira |
| 2005/0267454 A1 | 12/2005 | Hissong |
| 2005/0277970 A1 | 12/2005 | Norman et al. |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2006/0149225 A1 | 7/2006 | McClurken |
| 2007/0016185 A1 | 1/2007 | Tullis et al. |
| 2007/0049920 A1 | 3/2007 | Bloom et al. |
| 2007/0093808 A1 | 4/2007 | Mulier et al. |
| 2007/0112343 A1 | 5/2007 | Mische et al. |
| 2007/0118114 A1 | 5/2007 | Miller et al. |
| 2007/0149965 A1 | 6/2007 | Gallo, Sr. et al. |
| 2007/0156127 A1 | 7/2007 | Rioux et al. |
| 2007/0208332 A1 | 9/2007 | Mulier et al. |
| 2008/0004656 A1 | 1/2008 | Livneh |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0103494 A1 | 5/2008 | Rioux et al. |
| 2008/0146918 A1* | 6/2008 | Magnin ............... A61B 8/0841 600/437 |
| 2008/0207208 A1 | 8/2008 | Schutz |
| 2008/0234673 A1 | 9/2008 | Marion |
| 2008/0262489 A1 | 10/2008 | Steinke |
| 2009/0222001 A1 | 9/2009 | Greeley et al. |
| 2009/0264879 A1 | 10/2009 | Bloom et al. |
| 2009/0270896 A1 | 10/2009 | Sullivan et al. |
| 2009/0306655 A1 | 12/2009 | Stangenes |
| 2010/0069904 A1 | 3/2010 | Cunningham |
| 2010/0100095 A1 | 4/2010 | Bloom et al. |
| 2010/0160906 A1 | 6/2010 | Jarrard |
| 2010/0168743 A1 | 7/2010 | Stone et al. |
| 2010/0204560 A1 | 8/2010 | Salahieh et al. |
| 2010/0217255 A1 | 8/2010 | Greeley et al. |
| 2010/0241178 A1 | 9/2010 | Tilson et al. |
| 2010/0298763 A1 | 11/2010 | Adams et al. |
| 2011/0009856 A1 | 1/2011 | Jorgensen et al. |
| 2011/0028965 A1 | 2/2011 | McClurken |
| 2011/0118772 A1* | 5/2011 | Chen ............... A61B 17/12022 606/191 |
| 2011/0137298 A1 | 6/2011 | Nguyen et al. |
| 2011/0178515 A1 | 7/2011 | Bloom et al. |
| 2011/0190762 A1 | 8/2011 | Benn et al. |
| 2011/0196367 A1 | 8/2011 | Gallo |
| 2011/0224669 A1* | 9/2011 | Podany ............... A61B 18/1233 606/48 |
| 2011/0295249 A1 | 12/2011 | Bloom et al. |

(56) References Cited

U.S. PATENT DOCUMENTS

| | | |
|---|---|---|
| 2011/0301578 A1 | 12/2011 | Muniz-Medina et al. |
| 2011/0319889 A1 | 12/2011 | Conley et al. |
| 2012/0004657 A1 | 1/2012 | Conley et al. |
| 2012/0221035 A1 | 2/2012 | Harvey |
| 2012/0071712 A1 | 3/2012 | Manwaring et al. |
| 2012/0095461 A1 | 4/2012 | Herscher et al. |
| 2012/0101496 A1 | 4/2012 | McClurken et al. |
| 2012/0116397 A1 | 5/2012 | Rencher et al. |
| 2012/0143293 A1 | 6/2012 | Mauch et al. |
| 2012/0151165 A1 | 6/2012 | Conley et al. |
| 2012/0157989 A1 | 6/2012 | Stone et al. |
| 2012/0184983 A1 | 7/2012 | Chang et al. |
| 2012/0191084 A1* | 7/2012 | Davison ............ A61B 18/1402 606/33 |
| 2012/0191117 A1 | 7/2012 | Palmer et al. |
| 2012/0253343 A1 | 10/2012 | McClurken et al. |
| 2013/0066310 A1 | 3/2013 | Manwaring |
| 2013/0158535 A1 | 6/2013 | Denis et al. |
| 2013/0197502 A1 | 8/2013 | Manwaring et al. |
| 2014/0188105 A1 | 7/2014 | Conley et al. |
| 2016/0317209 A1* | 11/2016 | Cosmescu ............ A61B 17/32 |

FOREIGN PATENT DOCUMENTS

| | | |
|---|---|---|
| JP | 2009/504313 | 2/2009 |
| JP | 2008295905 | 3/2015 |
| WO | 96/37156 | 11/1996 |
| WO | 97/23169 | 7/1997 |
| WO | 98/38932 | 9/1998 |
| WO | 2007/037785 | 4/2007 |
| WO | 2010/141417 | 9/2010 |

OTHER PUBLICATIONS

International Search Report and Written Opinion dated Nov. 8, 2010 for PCT Appln No. PCT/US2010/048115, filed Sep. 8, 2010, 15 pages.

Partial Translation of Japanese Patent Laid-Open No. S62-204739.

International Search Report and Written Opinion, dated Mar. 30, 2017, PCT App. No. PCT/US2016/067101, filed Dec. 16, 2016, 25 pages.

* cited by examiner

ELECTROSURGICAL DEVICE WITH MULTIPLE MONOPOLAR ELECTRODE ASSEMBLY

CROSS-REFERENCE TO RELATED APPLICATION

This Non-Provisional Utility Application claims benefit to U.S. Provisional Application No. 62/269,235, filed Dec. 18, 2015, titled "ELECTROSURGICAL DEVICE WITH MONOPOLAR ELECTRODE ASSEMBLY" the entirety of which incorporated herein by reference.

BACKGROUND

This disclosure relates generally to the field of medical devices, systems and methods for use in surgical procedures. More specifically, this disclosure relates to electrosurgical devices, systems and methods that provide for cutting, coagulation, hemostasis, or sealing of bodily tissues including bone with an electrosurgical device.

Electrosurgery includes such techniques as cutting, coagulation, hemostasis, and/or sealing of tissues with the aid of electrodes energized with a suitable power source. Typical electrosurgical devices apply an electrical potential difference or signal between an active electrode and a return electrode on a patient's grounded body in a monopolar arrangement or between an active electrode and a return electrode on the device in bipolar arrangement to deliver electrical energy to the area where tissue is to be affected. The electrosurgical devices are typically held by the surgeon and connected to the power source, such as an electrosurgical unit having a power generator, via cabling.

Electrosurgical devices pass electrical energy through tissue between the electrodes to provide coagulation to control bleeding and hemostasis to seal tissue. Electrosurgical devices can also cut tissue through the use of plasma formed on the electrode. Tissue that contacts the plasma experiences a rapid vaporization of cellular fluid to produce a cutting effect. Typically, cutting and coagulation are often performed with electrodes in the monopolar arrangement while hemostasis is performed with electrodes in the bipolar arrangement.

Electrical signals can be applied to the electrodes either as a train of high frequency pulses or as a continuous signal typically in the radiofrequency (RF) range to perform the different techniques. The signals can include a variable set of parameters, such as power or voltage level, waveform parameters such as frequency, pulse duration, duty cycle, and other signal parameters that may be particularly apt or preferred for a given technique. For example, a surgeon could cut tissue using a first RF signal having a set of parameters to form plasma and control bleeding using a second RF signal having another set of parameters more preferred for coagulation. The surgeon could also use electrodes in a bipolar arrangement or a bipolar electrosurgical device for hemostatic sealing of the tissue that would employ additional RF signals having another set of parameters.

Historically, two distinct electrosurgical devices, one monopolar and the other bipolar, were used to perform different functions in surgery, such as tissue cutting and coagulating and tissue sealing. For example a surgeon would use a monopolar electrosurgical device to cut and coagulate tissue and use a bipolar electrosurgical device to seal the tissue. When different techniques or functions were performed during a surgical procedure, surgeons would switch between different devices. Switching between devices can lead to undesirable effects such as longer procedure times, longer response times to issues that unexpectedly develop during surgery, higher costs, and an increased likelihood of inaccuracy or imprecision.

To address these issues, some electrosurgical devices capable of performing multiple techniques such as cutting and coagulating tissue or cutting, coagulating, and sealing tissue, including fluid-assisted sealing of tissue, have been developed. Several such electrosurgical device are described, for example, in U.S. Pat. No. 8,632,533 to Greeley, et al., U.S. Patent Application Publication No. 2012/000465 to Conley, et al., U.S. Patent Application Publication No. 2011/0178515 to Bloom et al., each assigned to the assignee of the present disclosure and incorporated by reference herein in their entireties to the extent they are not inconsistent with the present disclosure.

Several devices that have been developed include a hand piece having two electrodes. These devices can be configured as bipolar electrodes connected to a source of bipolar power to operate in a bipolar mode, for example to seal tissue. To operate the same two-electrode device in a monopolar mode, for example to cut tissue, one of the two electrodes may be selectively deactivated and the other of the two electrodes coupled to a source of monopolar power. In this manner, the multiple function device may provide treatment to tissue utilizing one or both electrodes depending upon the desired tissue treatment.

Despite having the ability to perform different functions with a single device, when monopolar function is desired only one of the two electrodes of the device are utilized and the deactivated second electrode may obstruct the view of the surgeon during the monopolar operation. Furthermore, the deactivated electrode may unnecessarily prevent the monopolar electrode from entering smaller spaces or tissue areas that could otherwise be accessed if the unused electrode was not exposed. Further still, devices may not perform similarly to independent bipolar and monopolar devices.

SUMMARY

This summary is provided to introduce a selection of concepts in a simplified form that are further described below in the Detailed Description.

In one aspect, the disclosure relates to an electrosurgical device having a handpiece including a controller and an electrode assembly extending from the handpiece. The electrode assembly includes a monopolar blade and a monopolar electrode. The monopolar blade includes a conductive element partially coated with an insulator and electrically coupled to the controller to selectively deliver a monopolar radiofrequency (RF) cutting signal. The monopolar electrode is spaced apart and electrically isolated from the monopolar blade. The monopolar electrode includes an exposed major conductive surface electrically coupled to the controller to selectively deliver a monopolar RF hemostatic sealing signal with a dispersed fluid. In one example, the controller includes a pushbutton to electrically couple the monopolar blade to the monopolar electrode before electrically coupling the monopolar RF hemostatic sealing signal to the monopolar electrode.

In one aspect, the disclosure relates to an electrosurgical device having a handpiece and an electrode assembly extending from the handpiece. The electrosurgical device is configured to be used with an electrosurgical generator unit and a return electrode. The electrode assembly includes an electrically insulative intermediate component coupled to, and electrically isolating, a monopolar blade and a monopolar electrode. The monopolar blade and monopolar electrode can be configured as active electrodes in a monopolar arrangement. The electrosurgical device is configured to deliver a monopolar RF signal for cutting and a monopolar RF signal for coagulating to the monopolar blade. The electrode assembly is also configured to disperse a fluid, such as saline, and deliver a monopolar RF signal for hemostatic sealing with the monopolar electrode.

In one aspect, the disclosure relates to an electrosurgical device having a handpiece including a controller. A shaft extends from the handpiece. The shaft includes a hypotube configured to deliver a fluid and includes a conductive element. An electrode assembly extends from the shaft. The electrode assembly includes a monopolar blade and a monopolar electrode. The monopolar blade includes a conductive element partially coated with an insulator and electrically coupled to the controller to selectively deliver a monopolar radiofrequency (RF) cutting signal. The monopolar electrode is spaced apart and electrically isolated from the monopolar blade. The monopolar electrode includes an exposed major conductive surface electrically coupled to the controller via the conductive element to selectively deliver a monopolar RF hemostatic sealing signal with a dispersed fluid via the hypotube. In one example, the shaft has a variable length, and the hypotube includes an extendable and yieldably collapsible coil segment.

The monopolar blade in one example desiccates tissue with the monopolar RF signal for cutting via plasma. The creation of plasma to cut tissue includes producing a very high current density in the monopolar blade. In the monopolar arrangement, the active electrode is generally much smaller than the return electrode to allow the plasma to form at the active electrode and not at the return electrode. In order to further increase the current density, reduce the power used to cut tissue in the monopolar arrangement, or a combination of both, the monopolar blade may include a conductive element such as stainless steel partially coated with an electrically insulative material such as glass or ceramic to leave a small exposed area of the conductive element to create the plasma on the monopolar blade. The glass or ceramic insulator also serves as a thermal shield, which reduces the heat on the outer surface of the monopolar blade in the locations of conductive element covered with the insulator, to protect areas of tissue from thermal damage.

The conductive element and insulative coating cooperate to form a sturdy, substantially sized cutting blade having only a fraction of the conductive surface area of a similarly sized metal blade to increase the current density and reduce the size of a thermal damage zone. Thus, the monopolar conductive element serves to harness and focus the monopolar energy allowing it to create plasma for precise dissection and coagulation with reduced power, a higher current density at the conductive element, or a combination of reduced power and higher current density than available in a similarly sized metal blade.

The monopolar electrode is configured from an uncoated metal to be substantially larger in conductive surface area than the monopolar blade. The monopolar electrode is configured to avoid creating plasma, and to produce a relatively low current density, with the monopolar RF signal for hemostatic sealing. Furthermore, the monopolar electrode of the examples is configured with a fluid port to disperse a fluid for hemostatic sealing. In one example, an electrically conductive hypotube is electrically coupled to the monopolar electrode and fluidly coupled to the fluid port to deliver the monopolar RF signal for hemostatic sealing to the monopolar electrode and to disperse an energized conductive fluid. The intermediate component electrically insulates the monopolar electrode and hypotube from the monopolar blade.

The electrode assembly can be readily fabricated on a large scale. In one example, the hypotube is welded to the monopolar electrode, which are overmolded with an electrically insulative plastic, such as polytetraflouroethylene (PTFE) based material or others, to form the intermediate component. The monopolar blade is attached to the intermediate component. The electrode assembly can be electrically coupled to a controller, fluidly coupled to tubing, and welded to a shaft of a handpiece to form the electrosurgical device.

The monopolar blade can be specifically configured for cutting or desiccating tissue and operated with cutting and coagulating RF energy, which is performed with a relatively high impedance electrode and a high current density to form plasma. The monopolar electrode can be specifically configured to perform the techniques of hemostatic tissue sealing, which is performed with a relatively lower impedance electrode and a lower current density and a dispersed fluid. Thus, a clinician can perform multiple electrosurgical functions without having to change devices, or from monopolar to bipolar mode or vice versa.

DETAILED DESCRIPTION

Figure 1:
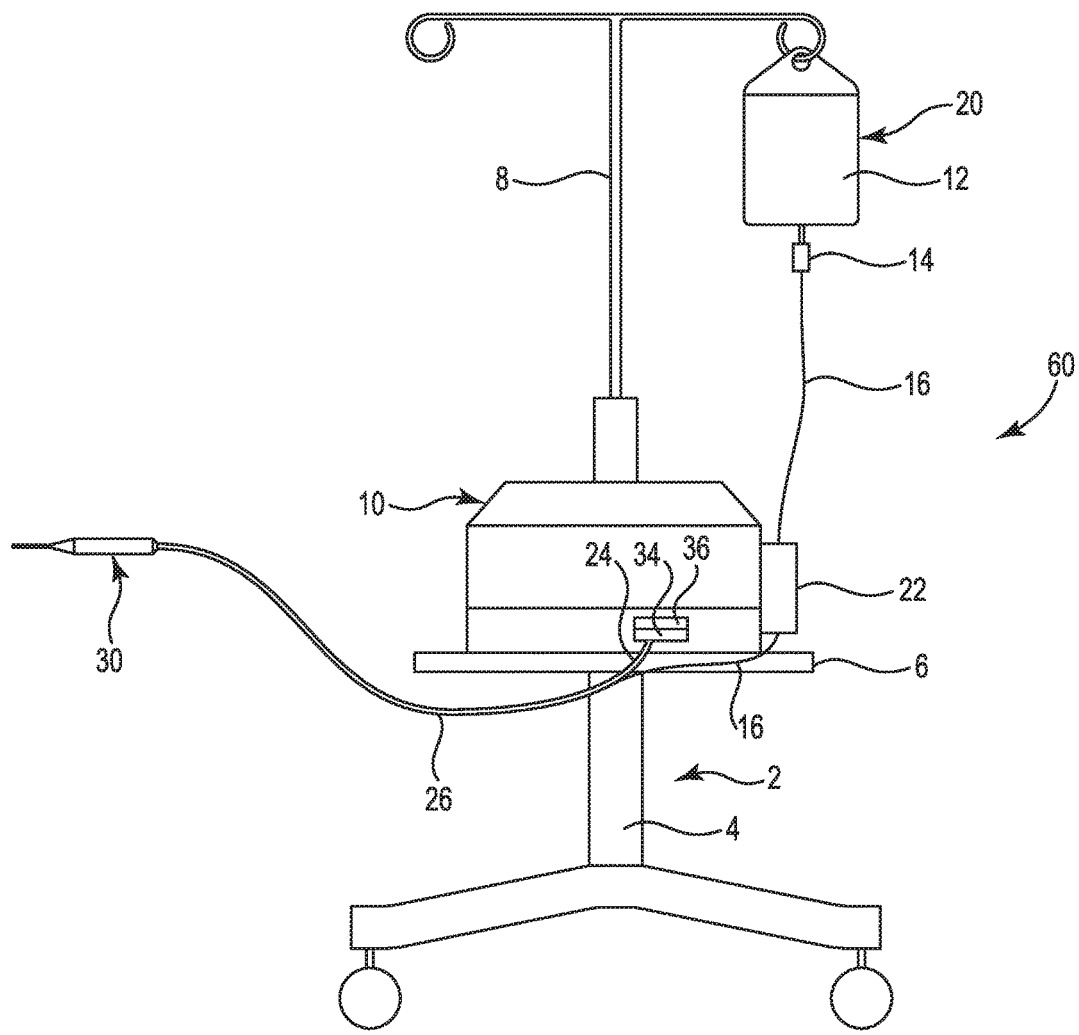
FIG. 1 is a front view illustrating an embodiment of a system according to the present disclosure including an example electrosurgical unit in combination with a fluid source and example handheld electrosurgical device.

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive. From the specification, it should be clear that the terms "distal" and "proximal" are made in reference to a user of the device.

FIG. 1 illustrates a front view of one example of a system 60 that includes an electrosurgical unit 10 in combination with an example handheld electrosurgical device 30. The device 30, in one example, can be configurable for use in cutting and sealing including electrocautery and coagulation in a first monopolar mode using a first monopolar electrode. In another example, device 30 can be configured to provide for hemostatic sealing of tissue including bone in a second monopolar mode using at least a second monopolar electrode in combination with a fluid source 20, or for other electrical surgical procedures.

The system 60 can be carried on a movable cart 2 having a support member 4 comprising a hollow cylindrical post which includes a platform 6 comprising a pedestal table to provide a flat, stable surface for location of the electrosurgical unit 10. Cart 2 can include a pole 8 having a height that can be adjusted by sliding the pole 8 up and down. Fluid source 20 can be supported at the top of pole 8.

Fluid source 20 may comprise a bag of fluid from which fluid 12 may flow through a drip chamber 14, to delivery tubing 16 and to handheld electrosurgical device 30. In one example, the fluid 12 includes saline and can include physiologic saline such as sodium chloride (NaCl) 0.9% weight/volume solution. Saline is an electrically conductive fluid, and other suitable electrically conductive fluids can be used. In other examples, the fluid may include a nonconductive fluid, such as deionized water, which may still provide advantages over using no fluid and may support cooling of portions of electrosurgical device 30 and tissue or reducing the occurrence of tissue sticking to the electrosurgical device 30.

The fluid delivery tubing 16 in the example passes through pump 22 to convey fluid to the electrosurgical device 30 and control fluid flow. Pump 22 in one example is a peristaltic pump such as a rotary peristaltic pump or a linear peristaltic pump. A peristaltic pump can convey the fluid through the delivery tubing 16 by way of intermittent forces placed on the external surface of the delivery tubing. Peristaltic pumps are often applied during use of the electrosurgical device 30 because the mechanical elements of the pump places forces on the external surface of the delivery tubing and do not come into direct contact with the fluid, which can reduce the likelihood of fluid contamination. Other examples of system 60 might not include a pump, and fluid can be is provided to the electrosurgical device 30 via gravity.

The example electrosurgical unit 10 can provide at least one or more monopolar RF power outputs to a specified electrosurgical instrument such as electrosurgical device 30. In one example, the electrosurgical unit 10 can be used for delivery of RF energy to instruments indicated for cutting and coagulation of soft tissue and for delivery of RF energy concurrent with fluid to instruments indicated for hemostatic sealing and coagulation of soft tissue and bone. In one example, the electrosurgical unit 10 can be capable of simultaneously or separately powering specified monopolar electrodes.

During monopolar operation of electrosurgical device 30, an active electrode is provided with electrosurgical device 30 while an indifferent, or neutral, electrode is provided in the form of a ground pad dispersive electrode located on a patient. For example, the ground pad dispersive electrode is typically on the back, buttocks, upper leg, or other suitable anatomical location during surgery. In such a configuration, the ground pad dispersive electrode is often referred to as a patient return electrode. An electrical circuit of RF energy is formed between the active electrode and the ground pad dispersive electrode through the patient. (In comparison, bipolar electrosurgical devices include a second electrode, often referred to as the return electrode providing a second electrical pole. The ground pad dispersive electrode is not used. An electrical circuit of RF energy is created between the first and second poles of a bipolar device. The current no longer flows through the patient's body to the ground pad dispersive electrode, but rather through a localized portion of tissue between the poles of the bipolar device.)

The electrosurgical device 30 in the example is connected to electrosurgical unit 10 via cable 24. Cable 24 includes plugs 34 that connect with receptacles 36 on the electrosurgical unit 10. In one example, a receptacle can correspond with an active electrode receptacle and one or more receptacles can correspond with controls on the electrosurgical device 30. Still further, a receptacle can correspond with a second active electrode receptacle. An additional cable may connect a ground pad electrode to a ground pad receptacle of the electrosurgical unit 10. In some examples, delivery tubing 16 and cable 24 are combined to form a single cable 26.

The features of electrosurgical unit 10 described are for illustration, and the electrosurgical units suitable for use with device 30 may include some, all, or other features than those described below. In one example, the electrosurgical unit 10 is capable of operating in at least monopolar mode as well as multiple functions within the monopolar mode such as a monopolar cutting function, a monopolar coagulation function, and monopolar hemostasis or tissue sealing function. In the monopolar cutting function, monopolar RF energy is provided to the device 30 at a first power level and/or a first waveform (collectively first, or cutting RF energy setting). For example, cutting RF energy for a cut function may be provided at a relatively low voltage and a continuous current (100% on, or 100% duty cycle). Nominal impedance can range between 300 to 1000 ohms for the cutting function. At a power setting of 90 Watts for cutting, voltage can range from approximately 164 to 300 volts root mean square (RMS). In the monopolar coagulation function, monopolar RF is energy is provided to the electrode at a second power level and/or second waveform (collectively second, or coagulating RF energy setting) that is different than at least one of the first power level or the first waveform. For example, coagulating RF energy for a coagulation function may be provided at a relatively higher voltage than the cut voltage and with a pulsed current, such as 1% to 6% on and 99% to 94% off, respectively (or 1% to 6% duty cycle). Other duty cycles are contemplated. The electrosurgical unit 10 may provide monopolar RF energy at a third power level and/or third waveform (collectively third, or hemostatic sealing RF energy setting) along with fluid for a (generally low voltage) hemostasis or tissue sealing function that may be the same as or different than the cutting and coagulating RF settings provided to the device 30 for the cut function or the coagulation function. In one example, hemostatic sealing energy can be provided with a continuous current (100% duty cycle). Nominal impedance can range between 100 to 400 ohms for the hemostatic sealing function. At a power setting of 90 Watts for hemostatic sealing, voltage can range from approximately 95 to 200 volts RMS.

In one example, the electrosurgical unit 10 provides RF energy to the active electrode as a signal having a frequency in the range of 100 KHz to 10 MHz. Typically this energy is applied in the form of bursts of pulses. Each burst typically has a duration in the range of 10 microseconds to 1 millisecond. The individual pulses in each burst typically each have a duration of 0.1 to 10 microseconds with an interval between pulses of 0.1 to 10 microseconds. The actual pulses are often sinusoidal or square waves and bi-phasic, that is alternating positive and negative amplitudes. Several other features are described in U.S. Pat. No.

8,323,276, to Palanker et al., and incorporated by reference herein in its entirety to the extent it is not inconsistent with the present disclosure.

The electrical surgical unit 10 includes a power switch to turn the unit on and off and an RF power setting display to display the RF power supplied to the electrosurgical device 30. The power setting display can display the RF power setting numerically in a selected unit such as watts.

The example electrosurgical unit 10 includes an RF power selector comprising RF power setting switches that are used to select or adjust the RF power setting. A user can push one power setting switch to increase the RF power setting and push the other power setting switch to decrease the RF power setting. In one example, power setting switches are membrane switches, soft keys, or as part of a touchscreen. In another example, the electrosurgical unit may include more than one power selectors such as a power selector corresponding with each of the different monopolar settings used in the different functions.

The example electrosurgical unit 10 can also include fluid flow rate setting display and flow rate setting selector. The display can include indicator lights, and the flow rate selector can include switches. Pushing one of the flow rate switches selects a fluid flow rate, which is than indicated in display.

While not being bound to a particular theory, the relationship between the variables of fluid flow rate Q (such as in units of cubic centimeters per minute (cc/min)) and RF power setting Ps (such as in units of watts) can be configured to inhibit undesired effects such as tissue desiccation, electrode sticking, smoke production, char formation, and other effects while not providing a fluid flow rate Q at a corresponding RF power setting Ps not so great as to disperse too much electricity and or overly cool the tissue at the electrode/tissue interface. Electrosurgical unit 10 is configured to increase the fluid flow rate Q generally linearly with an increasing RF power setting Ps for each of the three fluid flow rate settings of low, medium, and high.

Electrosurgical unit 10 can be configured to include control of the pump 22. In this example, the speed of the pump 22, and the fluid throughput, can be predetermined based on input variables such as the RF power setting and the fluid flow rate setting. In one example, the pump 22 can be integrated with the electrosurgical unit 10.

Several electrosurgical units, or generators, are described, for example, in U.S. patent application Ser. No. 14/927,999 to Smith, et al., titled RF Output Stage Switching Mechanism, filed Oct. 30, 2015; U.S. patent application Ser. No. 14/928,020 to Hubelbank, et al., titled Finger Switch Circuitry to Reduce Leakage Current, filed Oct. 30, 2015; U.S. patent application Ser. No. 14/927,969 to Smith, et al., titled Power Monitoring Circuitry and Method for Reducing Leakage Current in RF Generators, filed Oct. 30, 2015; and U.S. Patent Application Publication No. 2006/0149225 to McClurken, each assigned to the assignee of the present disclosure and incorporated by reference herein in their entireties to the extent they are not inconsistent with the present disclosure.

While electrosurgical device 30 is described with reference to electrosurgical unit 10 and other elements of system 60, it should understood the description of the combination is for the purposes of illustrating system 60. It may be possible to use the electrosurgical device 30 in other systems or the electrosurgical unit 10 may be used with other electrosurgical devices.

Figure 2:
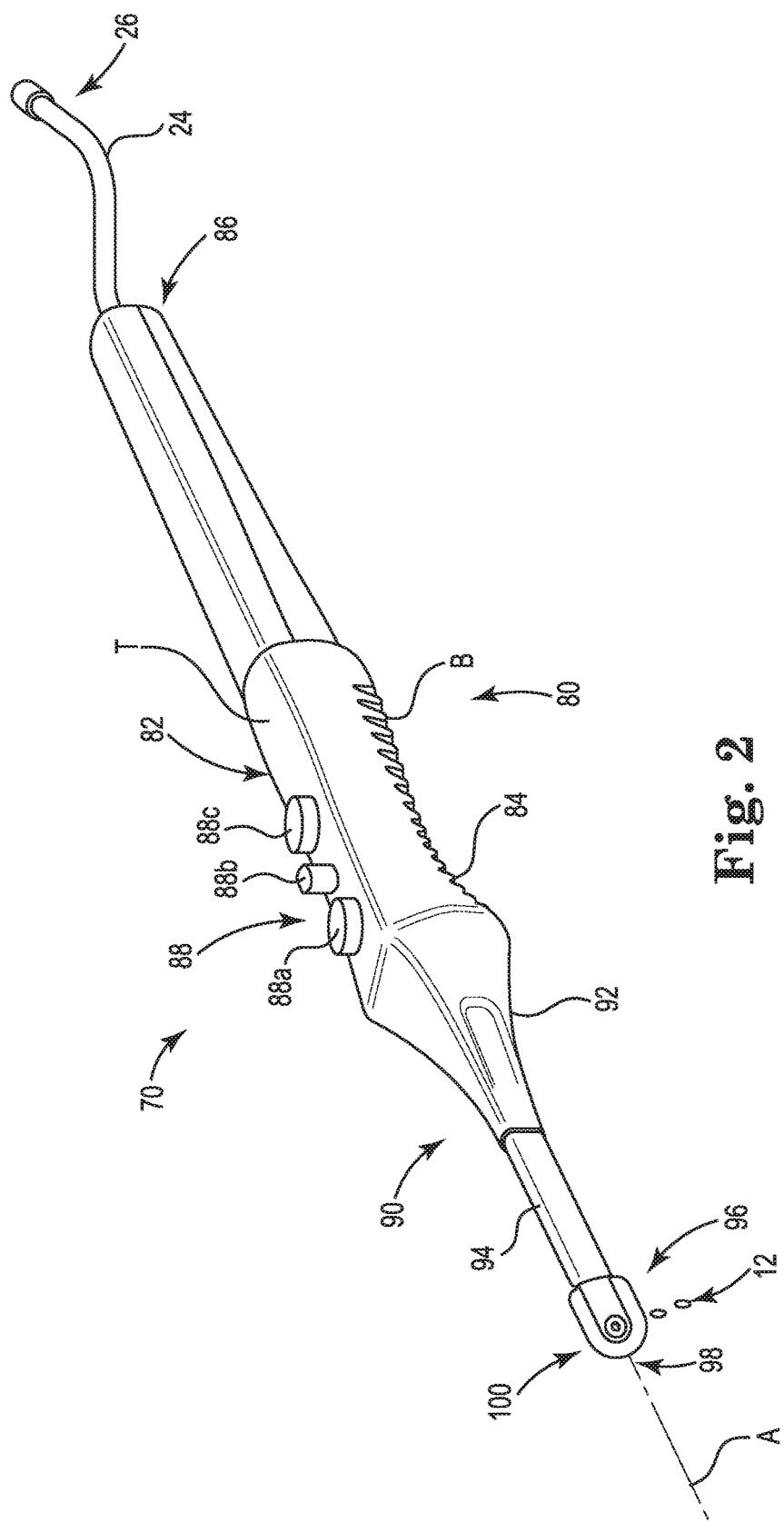
FIG. 2 is a perspective view illustrating an example of the electrosurgical device of FIG. 1 including a multiple monopolar electrode assembly.

FIG. 2 illustrates one example of an electrosurgical device 70, which can provide an example of electrosurgical device 30, having a multiple monopolar electrode assembly 100. In the example, the electrosurgical device 70 multiple monopolar electrode assembly 100 includes a first monopolar electrode configured in the example as a monopolar blade 102 operable to provide one or more functions in a monopolar mode, such as cutting and coagulation, and at least one or more monopolar electrodes 104 operable to provide additional functions in a monopolar mode, including hemostatic sealing of bone and tissue using a dispersed fluid, such as fluid 12.

Electrosurgical device 70 extending along longitudinal axis A includes a handpiece 80. Handpiece 80 includes a handle 82 having a finger grip portion 84 with ridges shown on the lower surface or bottom B of the device 70 and intended to be held in the surgeon's hand. The handpiece 80 includes a proximal end 86 for balance and, in the example, includes an electrical connector for electrically coupling cable 24 to the device 70.

Handpiece 80 may be configured to enable a user of electrosurgical device 70 to hold and manipulate device 70 between the thumb and index finger like a writing instrument or an electrosurgical pen. Handpiece 80 may comprise a sterilizable, rigid, electrically insulative material, such as a synthetic polymer (e.g., polycarbonate, acrylonitrile-butadiene-styrene). The handle 82 can include an upper surface, or top T, opposite bottom B. A controller 88, such as a set of one or more switches coupled to circuitry such as on a printed circuit board, in the example is disposed on top T and configured to be operated by the user's thumb or index finger to activate the electrode assembly 100.

The electrosurgical device 70 can include a probe assembly 90 extending distally from the handpiece 80. The probe assembly 90 in the example includes a body portion 92 attached to a shaft 94. The shaft 94, or other portions of electrosurgical device 70 may include one or more elements forming a subassembly to be generally one or more of rigid, bendable, fixed-length, variable-length (including telescoping or having an axially-extendable or axially-retractable length) or other configuration. An example of an electrosurgical device having a telescoping shaft is described in U.S. Patent Application Publication No. 2016/0120592 to Sylvester, et al. assigned to the assignee of the present disclosure and incorporated by reference herein in its entirety to the extent it is not inconsistent with the present disclosure. The shaft 94 carries one or more electrical conductors to a distal end 96 including the electrode assembly 100. The electrode assembly 100 includes a distal tip 98. Electrical pathways within the handpiece 80 and probe assembly 90 can be formed as conductive arms, wires, traces, other conductive elements, and other electrical pathways formed from electrically conductive material such as metal and may comprise stainless steel, titanium, gold, silver, platinum or any other suitable material. In the example, the shaft 94 includes a fluid lumen extending into the handpiece 80 for fluidly coupling to delivery tubing 16 in cable 26. The fluid lumen includes an outlet port 106 disposed on the electrode assembly 100 for selectively dispersing fluid 12.

In one example, the controller 88 includes one or more pushbuttons on the handle 82 in combination with circuitry such as a PCB within the electrosurgical device 70 to provide binary activation (on/off) control for each function. For example, one button 88a may be pressed to activate the monopolar blade 102 in a cut function, another button 88b may be pressed to activate the monopolar blade 102 in a coagulation function, and still another button 88c may be pressed to activate the monopolar electrode 104 and disperse fluid from port 106 in a sealing function and disperse fluid 12. Alternate configurations of the controller 88 and its activation are contemplated. In one example, the monopolar electrode 104 is not active (and fluid is not dispersed from fluid port 106) when cutting and coagulating RF energy is provided to the monopolar blade 102, but the monopolar blade 102 is active when hemostatic sealing RF energy is provided to the monopolar electrode 104.

The monopolar electrode 104 can be connected to the monopolar blade 102 when the activation button for one or more modes is depressed. Because the monopolar electrode 104 can be in contact with the tissue while the monopolar blade 102 is active, the monopolar electrode 104 in one example is configured to be isolated from the full output voltage of the electrical surgical unit 10. Also, the controller 88 can be configured to make two separate contacts such as a contact with high voltage isolation for the monopolar electrode 104, and on a contact with low voltage isolation for the controller 88.

Accordingly, the controller 88 can provide a controlled make and break order of electrical connections with one or more pushbuttons 88a, 88b, and 88c. A traditional micro switch may not provide isolation and using dual micro switches even if one has adequate isolation may be applied in an incorrect order. To over come these challenges, the controller 88 can include a dome switch to provide isolation and order. The dome switch is used for the low voltage connection and is affixed to the circuit board of the controller 88 with an insulative tape, such as with a polyimide tape available under the trade designation Kapton from DuPont of Wilmington, Del. A hole is provided in the tape over the dome switch to expose metal underneath. A lever, such as a conductive spring, is positioned above the dome so that it strikes the exposed metal of the dome centered on the hole in the tape. This conductive lever is then electrically connected via the circuit board to the monopolar electrode 104. An insulated button top, such as one of push buttons 88a, 88b, 88c, is then placed over the lever and the dome in such a manner that when the user depresses the button top the lever is first pressed into contact with the top of the dome electrically connecting the monopolar electrode 104 to the monopolar blade 102. In one example, the low force of the lever provides no tactile feedback to the user upon the first press. When the button top is further depressed, however, the dome snaps and makes the second contact, providing tactile feedback, as well as connecting activation wires to deliver a monopolar signal to the electrode assembly 100. When the button top is released, this process is reversed and the electrosurgical unit 10 turns off before the electrode assembly 100 is disconnected.

While electrode assembly 100 is described with reference to electrosurgical surgical device 70 and other elements of system 60, it should understood the description of the combination is for the purposes of illustrating one example of an electrosurgical device 30 having electrode assembly 100. It may be possible to use the electrode assembly 100 in other electrosurgical devices or with other systems using other electrosurgical units.

Figure 3:
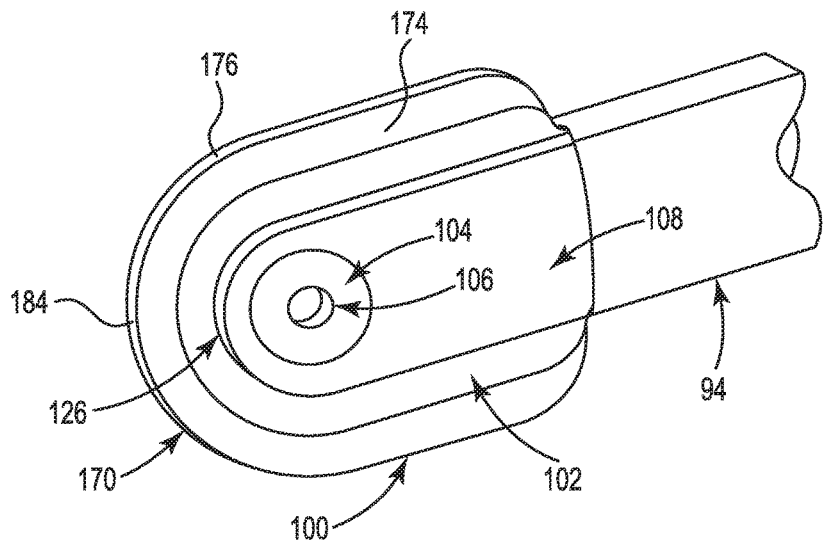
FIG. 3 is a close-up perspective view illustrating the electrosurgical device of FIG. 2 illustrating an example multiple monopolar electrode assembly.

FIG. 3 illustrates a close-up view of the distal end 96 of an electrosurgical device such as electrosurgical device 70. The electrode assembly 100 extends distally from shaft 94. Electrode assembly 100 includes monopolar blade 102 configured in the example as a relatively sharpened, high-impedance electrode blade for cutting and coagulating tissue with cutting and coagulating RF energy and monopolar electrode 104 configured as a relatively blunt, low-impedance conductor for hemostatic sealing of tissue and bone with a dispersed fluid using hemostatic sealing RF energy.

The distal tip 96 also includes a fluid port 106 in fluid communication with tubing 16 for dispersing fluid 12. In the example, the monopolar electrode 104 includes the fluid port 106. The monopolar blade 102 is spaced-apart and electrically insulated from monopolar electrode 104 via an electrically insulative intermediate component 108.

Figure 4:
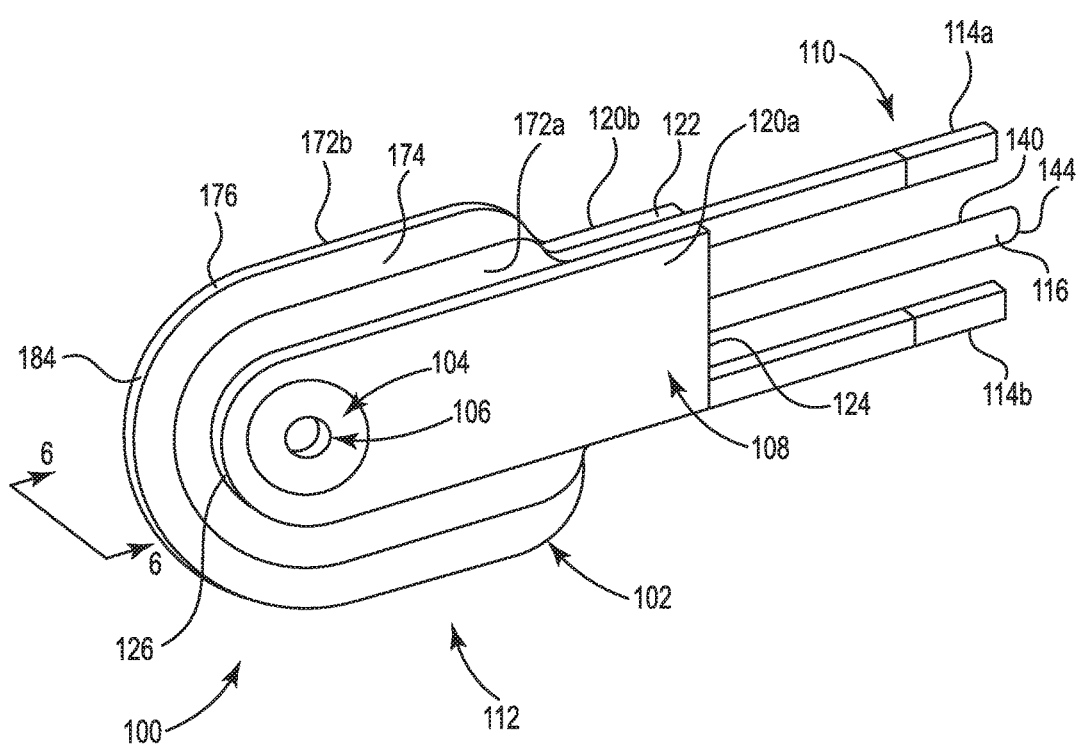
FIG. 4 is a perspective view illustrating the multiple monopolar electrode assembly of FIG. 3.

FIG. 4 illustrates an example of the electrode assembly 100. The electrode assembly 100 can includes tail portion 110 configured to be attached to or disposed within the shaft 94, and an active portion 112 configured to extend distally from the shaft 94 and engage tissue.

Tail portion 110 in the example includes one or more electrical conductors, such as arms 114a, 144b, electrically coupled to the monopolar blade 102 and configured to be operably coupled to the controller 88 to provide cutting and coagulation RF energy to the monopolar blade 102 when activated. The tail portion 110 also includes hypotube 116 in fluid communication with fluid port 106 and tubing 16 for delivering fluid 12 to the active portion 112 and dispersing fluid 12 from the fluid port 106. In the example, hypotube 116 is electrically conductive or includes an electrically conductive portion such as a wire or trace that is operably coupled to electrode 104 and configured to be operably couple to the controller 88 to provide hemostatic sealing RF energy to the electrode 104 when activated. The hypotube 116 in the example is electrically isolated from the arms 114a, 114b. In one example, the arms 114a, 114b and hypotube 116 can be electrically coupled to the controller 88 using wires or other electrical leads in the shaft 94 or elsewhere in the electrosurgical device 70 via a spot weld or other connection so as to conduct electrical energy from the controller 88 to electrode assembly 100. Hypotube 116 and arms 114a, 114b are held spaced-apart from each other with the intermediate component 108.

The intermediate component 108 can be formed from an insulative material such as a high temperature micromolded polymer. Examples insulative materials can include polytetrafluoroethylene (PTFE), polycarbonate (PC), polyoxymethylene (POM or acetal), or polyether ether ketone (PEEK). Intermediate portion 108 includes first and second side surfaces 120a, 120b defining an edge 122 and an end 124. The example intermediate component 108 includes a rounded tip 126.

Figure 5:
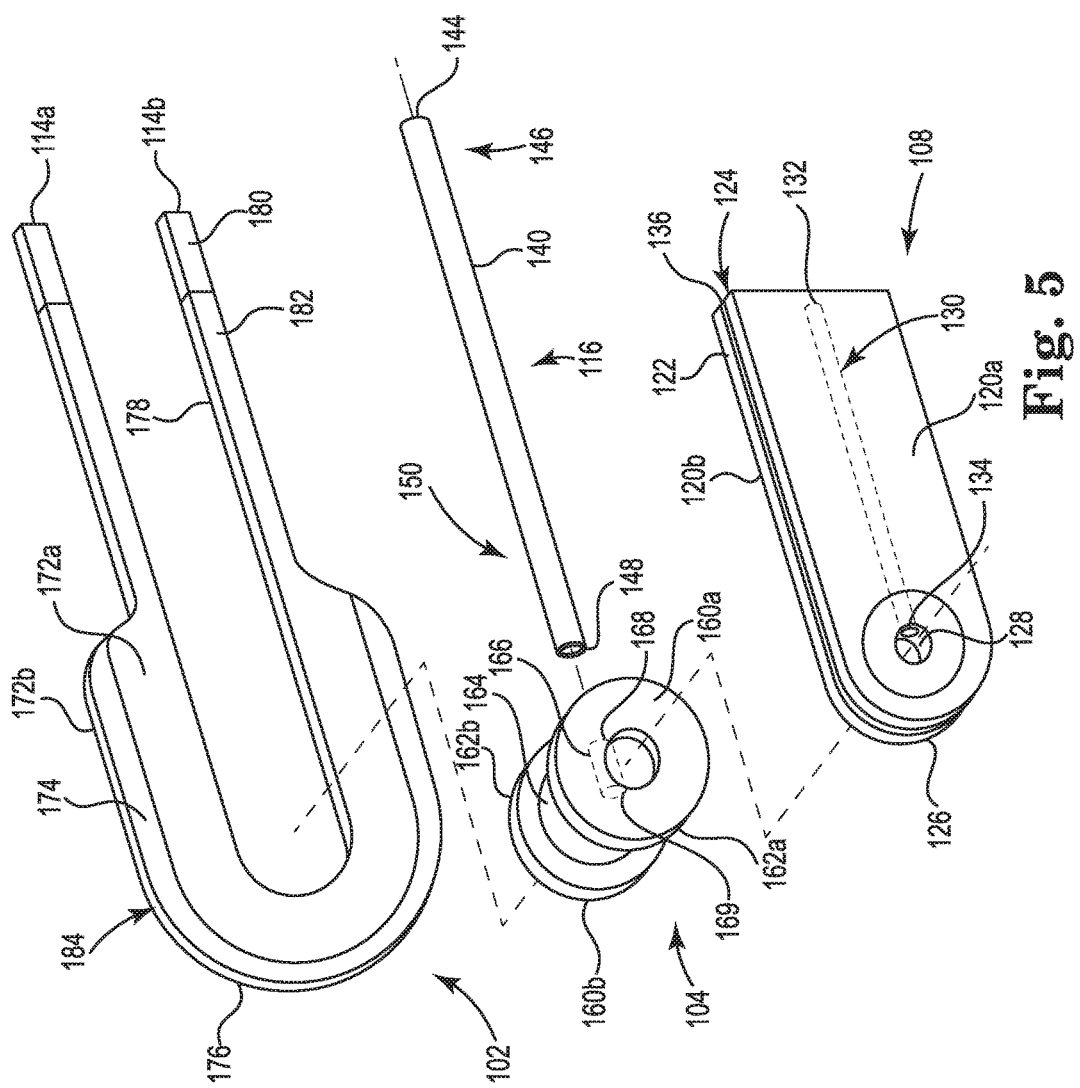
FIG. 5 is an exploded view illustrating the multiple monopolar electrode assembly of FIG. 3.

FIG. 5 illustrates an exploded view of the example electrode assembly 100 including the monopolar blade 102, monopolar electrode 104, hypotube 116, and intermediate portion 108. The intermediate component 108 includes an aperture 128 configured to receive the monopolar electrode 104. The intermediate portion 108 also includes a bore 130 having a proximal opening 132 on the end 124 and a distal opening 134 in the aperture 128 configured to receive the hypotube 116. Edge 122 of the intermediate component 108 includes a recessed groove 136 configured to received and hold the monopolar blade 102.

Figure 6:
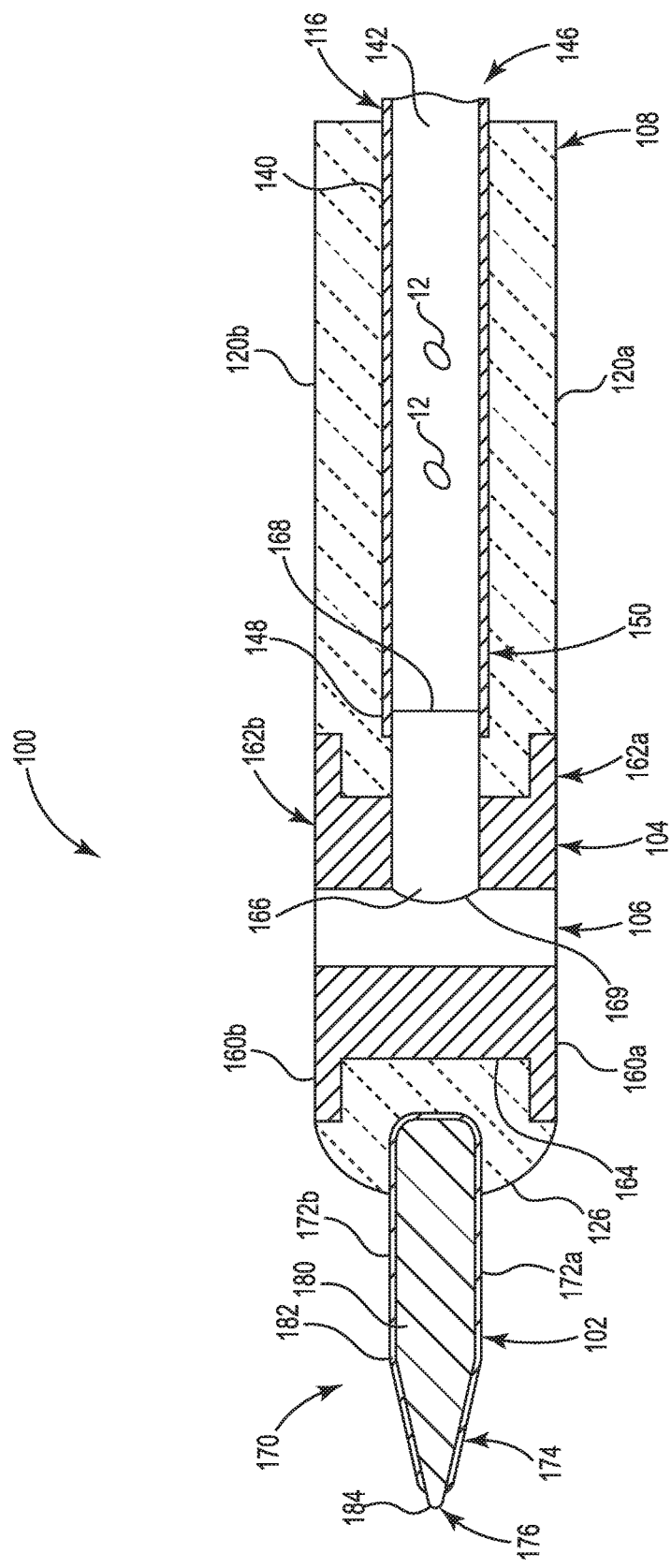
FIG. 6 is a top view illustrating a cross section of the multiple monopolar electrode assembly of FIG. 3.

FIG. 6 illustrates a top view of a cross section of the example electrode assembly 100 of FIG. 4 taken along lines 6-6. The hypotube 116 is configured from a medical grade material suitable for saline, or other appropriate liquid, delivery. In one example, the hypotube 116 is also electrically conductive, or includes an electrically conductive portion (such as a sleeve, trace, or wire) and can be constructed from a stainless steel. The hypotube 116 includes an axially extending wall 140 forming a lumen 142 and includes an inlet 144 on a proximal end 146 and an outlet 148 on a distal end 150. The proximal end 146 is configured to extend proximally from the intermediate portion 108, as indicated in FIG. 3. The proximal end 146 of wall 140 can be coupled to a fluid lumen (not shown) within the handpiece 80 to fluidly couple the inlet 144 to the delivery tubing 16 for receiving the fluid 12 into the hypotube 116. Further, the proximal end 146 of wall 140 (or conductive sleeve) can be electrically coupled to the controller 88 to receive hemostatic sealing RF energy. The distal end 150 of the wall 140 (or conductive sleeve) can be electrically coupled to the monopolar electrode 104.

FIGS. 4 and 5 illustrate the active portion 112 of electrode assembly 100 includes a cutting blade 170 of the monopolar blade 102 and the monopolar electrode 104.

The monopolar electrode 104 can be formed from a conductive material such as stainless steel. In the example, the monopolar electrode 104 includes first and second major exposed conductive surfaces 160a, 160b, disposed on sides 120a, 120b, of the intermediate component 108. The major exposed conductive surfaces 160a, 160b are configured to engage tissue and bone and to deliver hemostatic sealing RF energy.

FIG. 6 illustrates major exposed conductive surfaces 160a, 160b are generally opposite each other on opposing discs 162a, 162b on either ends of an axially transverse conductive rod 164. In one example, the major exposed conductive surfaces 160a, 160b are generally flush with the side surfaces 120a, 120b of the intermediate component 108. In another example, the discs 162a, 162b extend longitudinally from the side surfaces 120a, 120b. Fluid port 106 is formed within discs 162a, 162b and rod 164, and extends as an opening from the first major conductive surface 160a to the second major conductive surface 160b in the illustrated examples. Rod 164 is received within aperture 128 of the intermediate portion 108 and includes an axially extending fluid passage 166.

The distal end 150 of the hypotube 116 is fluidly coupled to the rod 164 at the fluid passage 166. For example, the fluid passage 166 includes an inlet 168 in fluid communication with the lumen 142 of the hypotube 116, and the fluid passage includes an outlet 169 in fluid communication with the fluid port 106 such that the lumen 142 is in fluid communication with the fluid port 106. Fluid 12 from the delivery tubing 16 is passed into the handpiece 80 and into the hypotube 116 and from the hypotube into the rod 164 where it is dispersed from the fluid port 106 on the major conductive exposed surfaces 160a, 160b.

Additionally, monopolar electrode 104 is electrically coupled to the distal end 150 of the hypotube 116 to receive hemostatic sealing RF energy from the controller 88. The major conductive exposed surfaces 160a, 160b have a relatively large surface area to provide a relatively low impedance and low current density for the hemostatic sealing RF energy.

FIGS. 4 and 5 illustrate the cutting blade 170 of the monopolar blade 102 can be integrally formed with the arms 114a, 114b. Cutting blade 170 includes first and second major surfaces 172a, 172b forming a blade edge 174 around the perimeter 176 of the monopolar blade 102. The blade edge 174 can be sharp or tapered to mechanically dissect as well as electrosugically cut and coagulate tissue. As indicated in FIG. 5, the monopolar blade 102 can be horseshoe-shaped and includes an inner edge 178 that is connected to the recessed groove 136 on the edge 122 of the intermediate component 108.

In an example, the cutting blade 170 is formed from a conductive element 180 partially coated with an insulator 182 to expose a conductive cutting electrode 184 proximate the perimeter 176. By implementing the cutting electrode 184, the conductive element 180 and insulator 182 cooperate to form a sturdy, substantially sized cutting blade assembly having only a small fraction of the conductive surface area of a similarly sized fully exposed metal blade at the cutting electrode 184 to reduce the size of a thermal damage zone. Thus, the cutting blade 170 serves to harness and focus the monopolar energy allowing it to create plasma for precise dissection and coagulation with reduced power, a higher current density at the cutting electrode 184, or a combination of reduced power and higher current density than available in a similarly sized fully-exposed metal blade.

The conductive element 180 can be formed from a metal, such as stainless steel or titanium, and the insulator 182 can be formed of glass or ceramic. In one example, the conductive element 180 is formed from a ferritic and martensitic chromium alloy as in series 400 stainless steel, which also adheres well to a glass or ceramic coating. In one example, the conductive element 180 is series 420 stainless steel. The conductive element 180 can be machined, stamped, or etched out of a larger sheet of metal. The conductive element 180 can be honed to a sharp, tapered blade edge 174 on one or both sides 172a, 172b. In one example, the exposed conductive cutting electrode 184 includes a thickness of between about 1 micrometer and 100 micrometers. In some examples, the conductive element 180 can be coated with a glass or ceramic insulator 182, such as a glass enamel insulator 182, by dipping the conductive element 180 in liquid or molten glass and then annealing the glass prior to assembly. In one example, the insulator 182 has a thickness of between about half and three times the thickness of the exposed conductive cutting electrode 184. In one example, the width of the cutting blade 170 of monopolar blade 102, as measured in a direction from tail 114a to tail 114b, is more than twice the diameter of the major surfaces 160a, 160b of the monopolar blade 104.

In the illustrated example, the monopolar blade 102 includes a single conductive element 180 configured as the cutting blade 178. In some examples, however, the monopolar blade 102 can be formed of multiple pieces of conductive material and include separate electrodes that provide cut and coagulation functions, respectively, such as described in U.S. Pat. No. 8,414,572 to Davidson, et al., assigned to the assignee of the present disclosure and incorporated by reference herein in its entireties to the extent it is not inconsistent with the present disclosure.

Figure 7:
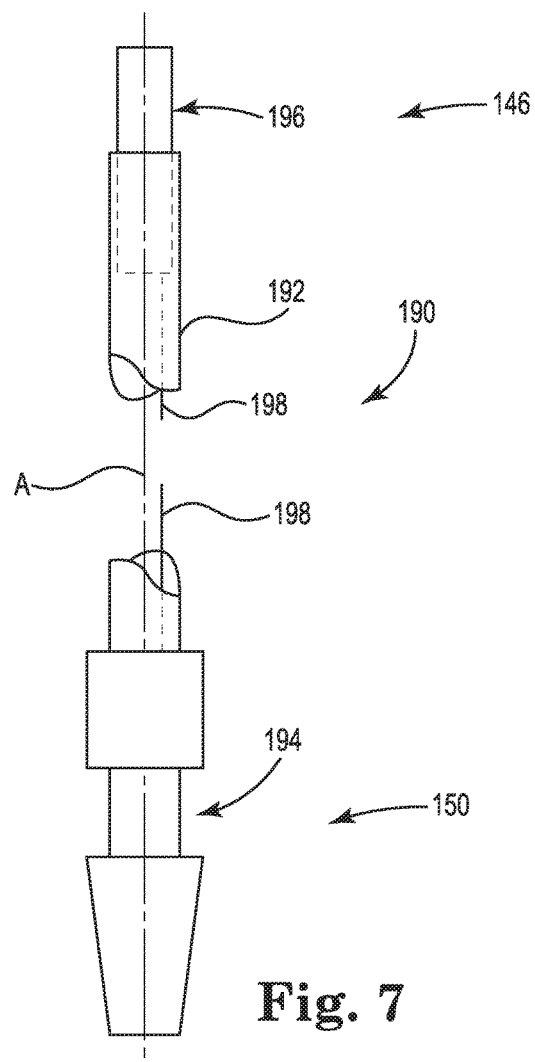
FIG. 7 is a close-up view illustrating an example of a hypotube for electrosurgical device of FIG. 2.

FIG. 7 illustrates an example hypotube 190 configured for use as hypotube 116 to deliver fluid 12 and RF energy from the handpiece 80 to the monopolar electrode 104. Hypotube 190 includes an axially extending hollow tubing 192, a proximal conductive terminal 194 (such as at the proximal end 150), a distal conductive terminal 196 (such as at the distal end 146), and a conductive element 198 extending axially to electrically couple the proximal conductive terminal 194 to the distal conductive terminal 196. In the example, the proximal conductive element 194 and distal conductive terminal 196 each include a lumen to allow fluid 12 to flow such that, when coupled to the hypotube 190, the fluid port 106 is in fluid communication with tubing 16. Additionally, the conductive element 198 electrically couples the proximal conductive terminal 194 to the distal conductive terminal 196 such that the controller 88 is in electrical communication with monopolar electrode 104 to provide hemostatic sealing RF energy to the electrode 104 when activated.

In the example, the proximal conductive terminal 194, distal conductive terminal 196, and conductive element 198 are configured from a conductive stainless steel. The proximal conductive terminal 194 can be configured to form a hollow barb-like fitting on tubing 192 that can mate with tubing 16, such as commonly used flexible tubing 16, such as polyvinyl chloride (PVC) tubing 16, to supply fluid 12 to the electrosurgical device 70 or electrode assembly 100. The distal conductive terminal 196 can be configured as a cylindrical tube partially disposed within tube 192 having a distally extending end coupled to the rod 164. The proximal conductive terminal 194 is electrically coupleable to the controller and the distal conductive terminal 196 is electrically coupleable to the rod 164 at inlet 168.

The tube 192 can be constructed from a non-conductive material such as PVC, PEEK, or a thermoplastic elastomer (TPE). In one example, the TPE is a polyether block amide (PEBA) available under the trade designation PEBAX from Arkema of Colombes, France. The conductive element 198 can be formed in the wall or tube 192 or can extend within the lumen of the tube 192 from the proximal conductive element 194 to the distal conductive element 196, such as a wire within the lumen.

Figure 8:
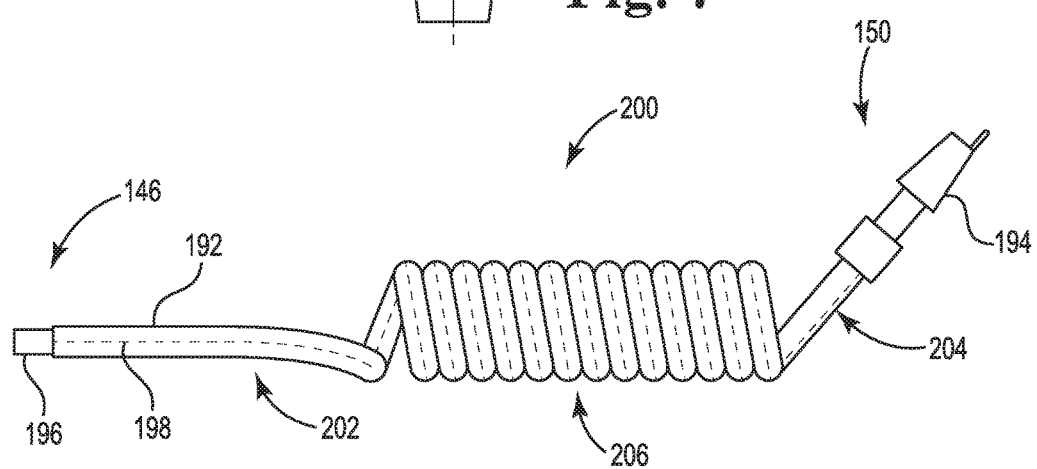
FIG. 8 is a side view illustrating an example of the hypotube of FIG. 7.

FIG. 8 illustrates an example hypotube 200, generally corresponding with hypotube 190 for use with, for example, an electrosurgical device 70 having a shaft 94 of selectably-variable length, such as axially extendable or axially retractable telescoping shaft such as an example of the telescoping device with saline irrigation line of U.S. Patent Publication No. 2016/0120592 described above. To translate axially, tube 192 and conductive element 198 flexible and are coiled to store the length for the hypotube 200 to extend and yieldably collapse within a selectively variable length shaft without slack, undue strain, or breakage in the fluid or electrical communication. Hypotube 200 includes a straight segment 202 including the distal conductive element 196, a tail segment 204 including the proximal conductive element 194, and an intermediate segment 206 wound into a coil. Conductive element 198 extends within the lumen of hypotube 200. In some examples, the straight segment 202 can be disposed within shaft 94 and coil of the intermediate segment 206 can be disposed within the body portion 92 or handpiece 80.

In some examples, the hypotube 200 can be formed from a stock piece of PEBA tubing. The length of the segments 202, 204, 206 can be selected by reference to dimensions of the electrosurgical device 70 including the length to fully extend and fully collapse. The time and temperature to shape and set the tubing can be selected based on various factors such as overall dimensions of the tubing, material used, stiffness of the coil desired, the propensity of the coil to lose shape after repeated extensions.

In one example of manufacturing electrode assembly 100, the monopolar blade 102, monopolar electrode 104, and hypotube 116 can be formed in separate processes and joined together. The hypotube 116 and monopolar electrode 104 can be welded together. The hypotube 116 joined with the monopolar electrode 104 can be overmolded with an electrically insulative material to form the intermediate component 108. The monopolar blade 102 can be attached to the intermediate component 108. The electrode assembly can be electrically coupled to a handpiece 80 and attached to the shaft 94. In one example, the electrode assembly can be attached to the shaft and handpiece of an electrosurgical device such as those sold under the trade designations PEAK PlasmaBlade 3.0, Peak PlasmaBlade 4.0, or similar products available from Medtronic Advanced Energy, LLC, of Minneapolis, Minn.

Although the present disclosure has been described with reference to preferred embodiments, workers skilled in the art will recognize that changes can be made in form and detail without departing from the spirit and scope of the present disclosure.

What is claimed is:

1. An electrosurgical device suitable for coupling to an electrosurgical unit, the electrosurgical device comprising:
    a handpiece having a controller, the controller to receive a monopolar radiofrequency (RF) cutting signal and a monopolar RF hemostatic sealing signal from the electrosurgical unit, the controller to provide selective activation of the monopolar RF cutting signal and the monopolar RF hemostatic sealing signal in the electrosurgical device; and
    an electrode assembly extending from the handpiece, comprising:
        a monopolar blade having a conductive element partially coated with an insulator, the monopolar blade electrically coupled to the controller to receive the monopolar RF cutting signal from the controller; and
        a monopolar electrode spaced apart and electrically isolated from the monopolar blade, the monopolar electrode having an exposed major conductive surface, the monopolar electrode electrically coupled to the controller to receive the monopolar RF hemostatic sealing signal from the controller with a dispersed fluid.

2. The electrosurgical device of claim 1 wherein the controller is configured to selectively deliver a monopolar RF coagulation signal to the monopolar blade.

3. The electrosurgical device of claim 1 wherein the controller includes a first button to selectively deliver the RF cutting signal and a second button to selectively deliver the RF hemostatic sealing signal.

4. The electrosurgical device of claim 1 where in the monopolar electrode includes a fluid port to disperse the fluid.

5. The electrosurgical device of claim 4 wherein the major conductive surface includes the fluid port to disperse the fluid.

6. The electrosurgical device of claim 4 comprising a hypotube having a tube in fluid communication with the fluid port configured to deliver the fluid and a conductive element in electrical communication with the controller and the monopolar electrode configured to deliver the monopolar RF hemostatic sealing signal.

7. The electrosurgical device of claim 6 wherein the tube forms a lumen and the conductive element is disposed within the lumen.

8. The electrosurgical device of claim 6 wherein the conductive element is a wire.

9. The electrosurgical device of claim 6 wherein the hypotube includes an extendable and yieldably collapsible coil segment.

10. The electrosurgical device of claim 1 wherein the electrode assembly extends from the handpiece via a shaft.

11. The electrosurgical device of claim 10 wherein the shaft is generally rigid and of a fixed length.

12. The electrosurgical device of claim 1 wherein the exposed major conductive surface is included in a plurality of exposed major conductive surfaces.

13. The electrosurgical device of claim 12 wherein the plurality of exposed major conductive surfaces are on opposites sides of the electrode assembly.

14. The electrosurgical device of claim 13 wherein the each of the major conductive surfaces include a fluid port to simultaneously deliver the fluid.

15. The electrosurgical device of claim 1 wherein the controller provides a selected order of electrical connections.

16. The electrosurgical device of claim 15 wherein the controller includes a pushbutton to electrically couple the monopolar blade to the monopolar electrode before electrically coupling the monopolar RF hemostatic sealing signal to the monopolar electrode.

17. An electrosurgical device suitable for coupling to an electrosurgical unit, the electrosurgical device comprising:
a handpiece having a controller, the controller to receive a monopolar radiofrequency (RF) cutting signal and a monopolar RF hemostatic sealing signal from the electrosurgical unit, the controller having a first setting to provide activation of the monopolar RF cutting signal and a second setting to provide activation of the monopolar RF hemostatic sealing signal in the electrosurgical device; and
an electrode assembly extending from the handpiece, the electrode assembly configured to deliver the monopolar RF cutting signal and the monopolar RF hemostatic sealing signal, the electrode assembly comprising,
an insulative intermediate component having a major surface and an edge,
a monopolar blade disposed on the edge of the intermediate component, the monopolar blade electrically coupled to the controller to receive the monopolar RF cutting signal from the controller, and
a monopolar electrode attached to the major surface of the intermediate component, the monopolar electrode electrically coupled to the controller to receive the monopolar RF hemostatic sealing signal from the controller with a dispersed fluid.

18. The electrosurgical device of claim 17 wherein the intermediate component includes a polymer.

19. The electrosurgical device of claim 17 wherein the monopolar blade includes a tapered cutting edge.

20. The electrosurgical device of claim 19 wherein the monopolar blade includes a conductive element partially covered with an electrically insulative coating.

21. The electrosurgical device of claim 20 wherein the electrically insulative coating is glass or ceramic.

22. The electrosurgical device of claim 17 wherein the monopolar electrode includes a fluid port to disperse the fluid.

23. The electrosurgical device of claim 22 comprising a conductive hypotube in fluid communication with the fluid port.

24. The electrosurgical device of claim 23 wherein the conductive hypotube is electrically coupled to the monopolar electrode and configured to deliver the monopolar RF hemostatic sealing signal to the monopolar electrode.

25. The electrosurgical device of claim 24 wherein the conductive hypotube includes a nonconductive wall portion in fluid communication with the fluid port and a conductive element in electrical communication with the monopolar electrode to deliver the monopolar RF hemostatic sealing signal to the monopolar electrode.

26. The electrosurgical device of claim 25 wherein the conductive element is a wire.

27. The electrosurgical device of claim 25 wherein the wall portion forms a lumen and the conductive element is disposed within the lumen.

28. The electrosurgical device of claim 25 wherein the hypotube includes an extendable and yieldably collapsible coil segment.

29. The electrosurgical device of claim 17 wherein the intermediate component electrically isolates the monopolar blade from the monopolar electrode.

30. An electrosurgical device suitable for coupling to an electrosurgical unit, the electrosurgical device comprising:
a handpiece having a controller, the controller to receive a monopolar radiofrequency (RF) cutting signal and a monopolar RF hemostatic sealing signal from the electrosurgical unit, the controller to provide activation of the monopolar RF cutting signal and the monopolar RF hemostatic sealing signal in the electrosurgical device;
a shaft extending from the handpiece, the shaft including a hypotube configured to deliver a fluid, the hypotube having a conductive element; and
an electrode assembly extending from the shaft, comprising:
a monopolar blade having a conductive element partially coated with an insulator, the monopolar blade electrically coupled to the controller to receive the monopolar RF cutting signal from the controller; and
a monopolar electrode spaced apart and electrically isolated from the monopolar blade, the monopolar electrode having an exposed major conductive surface, the monopolar electrode electrically coupled to the controller via the conductive element to receive the monopolar RF hemostatic sealing signal from the controller with a dispersed fluid via the hypotube.

31. The electrosurgical device of claim 30 wherein the hypotube includes a nonconductive wall portion in fluid communication with a fluid port on the major conductive surface.

32. The electrosurgical device of claim 31 wherein the conductive element is a wire.

33. The electrosurgical device of claim 32 wherein the wall portion forms a lumen and the conductive element is disposed within the lumen.

34. The electrosurgical device of claim 33 wherein the hypotube includes an extendable and yieldably collapsible coil segment.

35. The electrosurgical device of claim 30 wherein the shaft is generally rigid and of a fixed length.

* * * * *